United States Patent [19]

Ohmi

[11] Patent Number: 5,092,880
[45] Date of Patent: Mar. 3, 1992

[54] METHOD OF DETERMINING THE ASTIGMATIC POWER AND THE POWER FOR AN INTRAOCULAR LENS, FOR A TORIC INTRAOCULAR LENS

[76] Inventor: Genjiro Ohmi, Lui-shatore-Nakanoshima-901, 5-3-92 Nakanoshima, Kitaku, Osaka, Japan

[21] Appl. No.: 423,168

[22] Filed: Oct. 18, 1989

[30] Foreign Application Priority Data

Oct. 21, 1988 [JP] Japan .................................. 63-266789
Nov. 4, 1988 [JP] Japan .................................. 63-280212
Sep. 20, 1989 [JP] Japan .................................. 1-245871

[51] Int. Cl.⁵ .............................................. A61F 2/16
[52] U.S. Cl. ................................................... 623/6
[58] Field of Search ...................................... 623/6

[56] References Cited

U.S. PATENT DOCUMENTS

4,277,852 7/1981 Poler ........................................ 623/6
4,315,336 2/1982 Poler ........................................ 623/6
4,512,039 4/1985 Lieberman ............................... 623/6

FOREIGN PATENT DOCUMENTS 61-156915 9/1986 Japan .

OTHER PUBLICATIONS

*Clinical Optics,* Fannin et al., Butterworths, 1987, pp. V,31-35, 440.

*Primary Examiner*—Randy C. Shay
*Attorney, Agent, or Firm*—Jordan and Hamburg

[57] ABSTRACT

The astigmatic power for a toric intraocular lens which corrects the preoperative astigmatism of a patient due to a disease or the like can be determined by converting preoperative corneal astigmatic data to the intraocular lens astigmatic power. Furthermore, the intraocular lens power for a toric intraocular lens which corrects the preoperative corneal astigmatism of a patient due to a disease or the like can be determined by calculating the intraocular lens spherical and astigmatic powers from radius-of-corneal-curvature data or corneal refractive power data in the strong principal meridian direction and radius-of-corneal-curvature data or corneal refractive power data in the weak principal meridian direction.

7 Claims, 2 Drawing Sheets

METHOD OF DETERMINING THE ASTIGMATIC POWER AND THE POWER FOR AN INTRAOCULAR LENS, FOR A TORIC INTRAOCULAR LENS

BACKGROUND OF THE INVENTION

1. Technical Field

The present invention relates to a method of determining (1) the astigmatic power and (2) the power for an intraocular lens, for a toric intraocular lens to be inserted after extracapsular extraction in cataract surgery.

2. Background Art

In cataract surgery by extracapsular extraction, the nucleus of the crystalline lens is first removed by expression and an intraocular lens, which is an artificial lens, is then inserted into the posterior chamber for correction.

However, in the case of a patient with preoperative corneal astigmatism (which is referred to briefly as preoperative astigmatism) due to a disease, for instance, this preoperative astigmatism remains after operation.

To correct this astigmatism, it is common practice to use spectacles or hard contact lenses (hereinafter referred to briefly as HCL) or perform a refractive surgery such as relaxing incision.

However, spectacles and HCL are generally not effective enough to correct an astigmatism in excess of 3 diopters (diopter: hereinafter referred to as (D)) and, moreover, the very use of them is not comfortable to the patient.

Furthermore, the procedure of relaxing incision has the following disadvantages.

(1) In a patient who has undergone corneal incision and suturing in cataract surgery, a reoperation at the same site involves considerable technical difficulties.

(2) Since this operation is tantamount to the intentional creation of a trauma, the risk of corneal infection is increased.

(3) There is a risk for inducing an irregular astigmatism.

(4) This procedure, following cataract surgery, imposes considerable mental and physical burdens on the patient.

(5) It has been criticized as an ethically questionable conduct to intentionally injure the healthy cornea.

(6) While the astigmatic power varies from one individual to another, any correction made by the surgeon is based on his sensory or subjective judgement and may not be thorough correction.

It is for these reasons that the procedure of correcting an astigmatism by relaxing incision has not been commonly practiced.

Heretofore, several procedures for correcting corneal astigmatism with an intraocular lens have been proposed (e.g. U.S. Pat. No. 4,277,852 and Japanese laid-open Utility Model Publication 61-156,915. While this literature suggest that astigmatism can be corrected with an intraocular lens, it is reticent about an important question, namely how, in applying an intraocular lens to the patient, the spherical power and astigmatic power values are to be determined.

There has accordingly been proposed an intraocular lens for correcting the astigmatism induced during operation (hereinafter referred to briefly as operative astigmatism) which is predicated on a prediction of the degree of the corneal astigmatism which occurs as the geometry of the cornea is altered by incision of the sclerocorneal region and subsequent suturing (U.S. Pat. No. 4,512,039). With this intraocular lens, the operative corneal astigmatism can be corrected. However, since the preoperative astigmatism remains uncorrected, correction with spectacles or HCL is still necessary.

Furthermore, while this operative astigmatism is of the order of 0.5(D) at 3 to 6 postoperative months, there have been advances in surgical procedure to the extent that, in most patients, the operative astigmatism is completely eliminated in about one year after operation. Therefore, the incidence of operative astigmatism is not a serious problem today. The most important task is rather correction of preoperative astigmatism.

OBJECT OF INVENTION

The present invention has as its object to provide a method of determining (1) the astigmatic power and (2) the power for an intraocular lens, for a toric intraocular lens to be used for correction of preoperative astigmatism.

SUMMARY OF THE INVENTION

By the method of determining the astigmatic power for a toric intraocular lens in accordance with the present invention wherein preoperative corneal astigmatism data are converted to the astigmatic power of an intraocular lens, the preoperative corneal astigmatism can be successfully corrected with an intraocular lens.

To determine the intraocular lens power for a toric intraocular lens by the method of the invention, the spherical power P1 for the intraocular lens in the strong principal meridian direction is first calculated from the radius-of-corneal-curvature data R1 or corneal refractive power data K1 in the same direction and the spherical power P2 for the intraocular lens in the weak principal meridian direction is calculated from the radius-of-corneal-curvature data R2 or corneal refractive power data K2 in the same direction. Then, the spherical power P1 value in the strong principal meridian direction is subtracted from the spherical power P2 value in the weak principal meridian direction to find a cylindrical power P3.

Now, the strong principal meridian direction is taken as the axis of astigmatism, P1 as the spherical power of the intraocular lens and P3 as the astigmatic power of the intraocular lens.

To determine the intraocular lens power by the method for determining the intraocular lens power for a toric intraocular lens in accordance with the present invention, P1 and P2 are first determined and P2 is then subtracted from P1 to find P3 in the same manner as above. Then, the weak principal meridian direction is taken as the axis of astigmatism, P2 as the spherical power of the intraocular lens and P3 as the astigmatic power of the intraocular lens.

BRIEF DESCRIPTION OF DRAWINGS

FIG. 5 is a plan view showing the intraocular lens with its axis of astigmatism passing through the bases of haptics;

FIG. 6 is a plan view showing the intraocular lens with its axis of astigmatism passing through tabs; and FIG. 7 is a plan view showing the intraocular lens with its axis of astigmatism passing through markings.

DETAILED DESCRIPTION OF PREFERRED EMBODIMENTS

Figure 1:
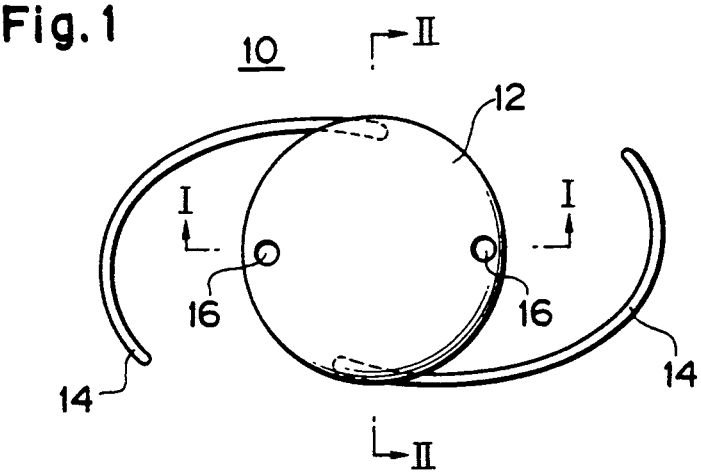
FIG. 1 is a plan view showing one embodiment of the invention.
Figure 2:
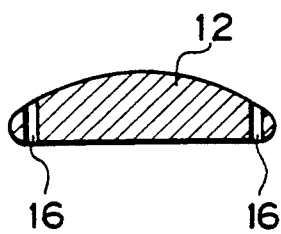
FIG. 2 is a sectional elevation view taken on the line I—I of FIG. 1.
Figure 3:
FIG. 3 is a sectional elevation view taken on the line II—II of FIG. 1.

One embodiment of the invention is described below, referring to the accompanying drawings.

The reference numeral 10 represents a toric intraocular lens. It is a sharing intraocular lens made of a high molecular weight compound such as polymethyl methacrylate (PMMA). The reference numeral 12 designates the optical zone of the intraocular lens, which is circular in planar configuration.

The reference numerals 14, 14 represent haptics, respectively, which project from the diametrically opposite positions of said optical zone 12.

The reference numerals 16, 16 represent positioning holes which are located in the marginal zone around said optical zone 12. The line interconnecting these two positioning holes 16, 16 passes through the center of the circle defining the optical zone 12.

The method of determining the intraocular lens power for the optical zone 12 of the above toric intraocular lens 10 for correction of preoperative astigmatism is described below. It should be understood that the term 'intraocular lens power' is used herein to mean a combination of the spherical power with the astigmatic power necessary for correction of astigmatism.

While there are several versions of this method for determining the intraocular lens power, the one using the Sanders-Retzlaff-Kraff formula (hereinafter referred to as the SRK formula) is first described.

Assuming that the spherical powers of the intraocular lens 10 are P1 and P2, $$P1 = A - 2.5L - 0.9K1 \quad (1)$$

$$P2 = A - 2.5L - 0.9K2 \quad (2)$$

$$K1 = \frac{1000(N-1)}{R1} \quad (3)$$

$$K2 = \frac{1000(N-1)}{R2} \quad (4)$$

where A: an intraocular lens constant, N: the refractive index of cornea, aqueous humor and vitreous body, L: axial length data (mm), K1: the corneal refractive power (D) in the strong principal meridian direction, K2: the corneal refractive power (D) in the weak principal meridian direction, R1: the radius-of-corneal-curvature data (mm) in the strong principal meridian direction, and R2: the radius-of-corneal curvature data (mm) in the weak principal meridian direction. Then, the astigmatic power P3 is determined as follows.

When the strong principal meridian direction is used as the axis of astigmatism, the cylindrical power found by subtracting P1 from P2 is taken as the astigmatic power P3.

When the weak principal meridian direction is used as the axis of astigmatism, the cylindrical power found by subtracting P2 from P1 is taken as the astigmatic power P3.

Based on the intraocular lens power thus determined, the optical zone 12 is constructed. Then, the intraocular lens 10 is inserted into the anterior chamber of the patient during operation.

Taking a case in which the measurement of corneal refractive power prior to cataract surgery revealed an astigmatism of 3(D) as an example, the intraocular lens power S for the intraocular lens 10 to be inserted for insuring a total astigmatism of 0(D) after 3 postoperative months is determined as follows.

First, the axial length L of the patient's eye is measured with an axial length ultrasound biometer (A scan) or the like.

Then, the radii of corneal curvature R1 and R2 are measured with an ophthalmometer, corneal topographic system or the like and the values of R1 and R2 thus found are substituted into the equations (3) and (4), respectively, to calculate the corneal refractive powers K1 and K2. It should be understood that the corneal refractive powers K1 and K2 may be directly measured with a corneal refractometer or the like.

It is assumed that L=23.2 (mm), K1=44(D) in 90° direction and K2=41(D) in 180° direction. Since the intraocular lens 10 is a posterior chamber lens, it is also assumed that the intraocular lens constant A=116.5.

Substituting L=23.2 (mm), K1=44(D) and A=116.5 into equation (1) gives P1=18.9(D).

Substituting L=23.2 (mm), K2=41(D) and A=116.5 into equation (2) gives P2=21.6(D).

Therefore, the intraocular lens power necessary for this patient is +18.9(D) in 90° direction and +21.6(D) in 180° direction. Thus, the parameters in this case are spherical power +18.9(D), astigmatic power +2.7(D), and axis of astigmatism 90° or spherical power +21.6(D), astigmatic power −2.7(D), and axis of astigmatism 180°. For simplication of power designations, 0.5(D) is used as the minimum unit. Thus, for example, +18.9(D) may be designated as +19.0(D) and 2.7(D) as +2.5(D).

Now, the procedure for setting the orientation of the axis of astigmatism is explained below. The following two conditions must be satisfied in setting the axis of astigmatism.

(1) The surgeon may easily ascertain the orientation of the axis of astigmatism in the operation.

(2) The axis of astigmatism must pass through the center of the circular optical zone 12.

To meet the above two conditions, the axis of astigmatism is set on the line interconnecting positioning holes 16, 16 in this embodiment (FIG. 1). By this setting procedure, the surgeon can easily ascertain the orientation of the axis of astigmatism and the axis of astigmatism passes through the center of the circle defining the optical zone 12. Furthermore, the optical zone 12 need not be provided with any special reference markings indicative of the axis of astigmatism and, therefore, the processing of the intraocular lens 10 is easier.

The relationship between this orientation of the axis of astigmatism and the astigmatic power of the intraocular lens is determined beforehand at the stage of determining the intraocular lens power.

Figure 4:
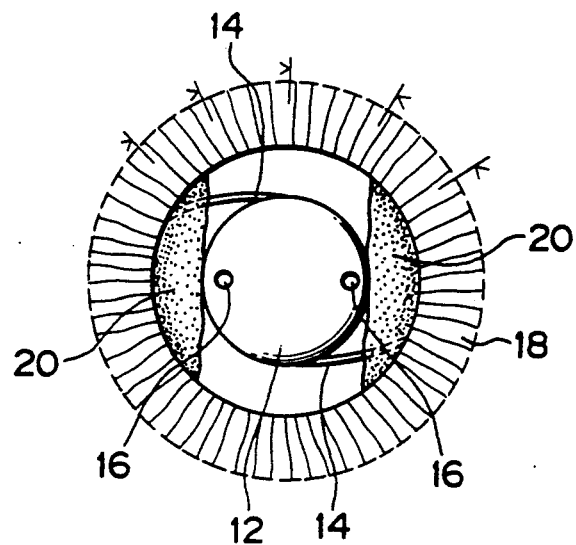
FIG. 4 is a plan view showing the intraocular lens set in the posterior chamber.

The intraocular lens 10 fabricated to the above settings is inserted into the posterior chamber by the usual surgical procedure. For example, the lens 10 can be inserted by any of compression, dialing and closed system techniques. Regarding the orientation of insertion of this intraocular lens 10, the weak principal meridian direction of the intraocular lens is aligned with the strong principal meridian direction of the cornea and the strong principal meridian direction of the intraocular lens is aligned with the weak principal meridian direction of the cornea. In FIG. 4 which shows the intraocular lens 10 inserted into the posterior chamber, the screrocorneal region and the anterior lens capsule are designated by the reference numerals 18 and 20, respectively.

The intraocular lens 10 thus inserted into the posterior chamber is locked in position as haptics 14, 14 are secured cicatricially in gaps between the ciliary processes or between the anterior and posterior lens capsules at the lens equator. Therefore, the optical part 12 is retained permanently in position without rotation. As a result, the axis of astigmatism of the intraocular lens 10 is fixed and the lens 10 corrects the astigmatism in the patient.

Therefore, it is no longer necessary for the patient to wear spectacles or HCL postoperatively, thus being freed from the pain and discomfort which were inevitable before. Another advantage is that the preoperative astigmatism due to a disease or the like can also be corrected. In addition, unlike the conventional procedure of relaxing incision, the method of this invention insures an accurate correction of the astigmatism power.

While the axis of astigmatism of the intraocular lens 10 is coincidental with the line interconnecting the positioning holes 16 and 16 in the above embodiment, the following alternative orientations may be adopted.

Figure 5:
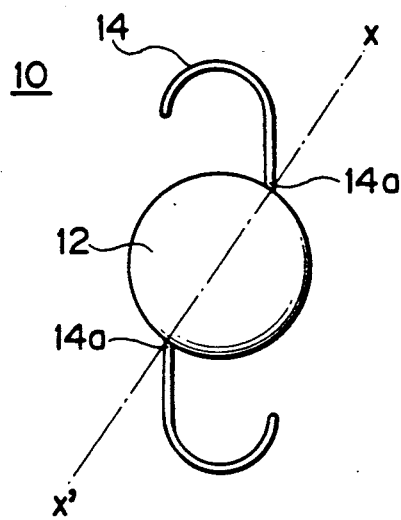
FIGS. 5 through 7 are plan views showing the intraocular lenses with different orientations of the axis of astigmatism.

(1) The line interconnecting the bases 14a, 14a of haptics 14, 14 secured to the optical zone 12 is used as the axis of astigmatism X—X' (FIG. 5).

Figure 6:
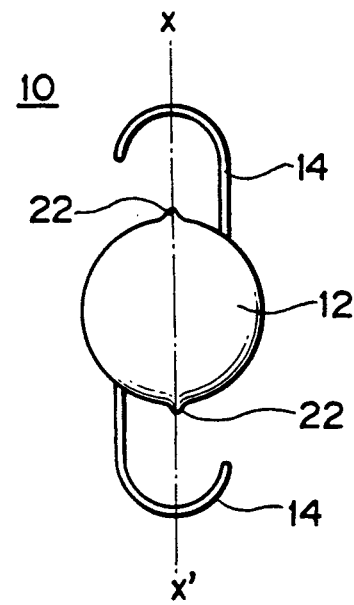

(2) The optical zone 12 is provided with identification tabs 22, 22 and these tabs are used as references for setting the axis of astigmatism X—X' (FIG. 6).

The above-mentioned tabs 22, 22 project outwards from diametrically opposite edges of the optical zone 12.

Figure 7:
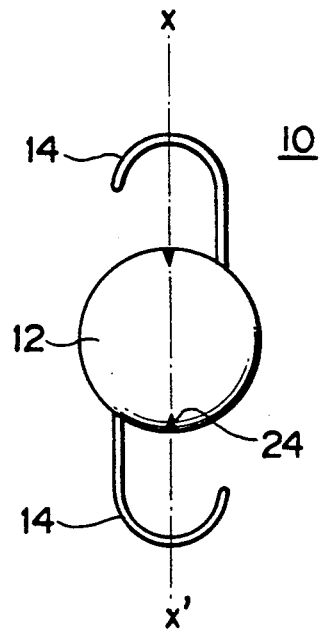

(3) The optical zone 12 is provided with color or laser-sculptured markings 24, 24 at its diametrically opposite edges and the line interconnecting the markings 24, 24 is used as the axis of astigmatism X—X'; (FIG. 7).

Each of these three methods satisfies the above-mentioned two conditions, i.e. that the surgeon can easily ascertain the orientation of the axis of astigmatism during operation and that the axis of astigmatism passes through the center of the optical zone 12. Of the above three alternative methods, the first method (1) is particularly advantageous, for since it does not require special identification marks for the axis of astigmatism, the processing of the intraocular lens is facilitated.

Furthermore, although the intraocular lens 10 described above is a sharing type lens, the effects of the invention can also be obtained when the method for setting the axis of astigmatism according to this embodiment is applied to the optical zone of any other posterior or anterior lens, inclusive of a pierce-type lens. In such cases, all the modification required is to change the value of intraocular lens constant A in the equations (1) and (2). For example, this value may be A=114.5–116.0 for an anterior chamber lens, A=115.0–116.5 for an iris-supported lens, and A=116.0–120.0 for a posterior chamber lens.

While, in the above embodiment, the SRK formula is used to compute the intraocular lens power for a patient with preoperative corneal astigmatism, the intraocular lens power for a toric intraocular lens can be computed by various theoretical formulas as described below.

In a first procedure, the formula of R. D. Binkhorst is used. Thus, the spherical powers P1 and P2 are first calculated by means of equations (5) and (6).

$$P1 = \frac{1000N(N \cdot R1/0.3333 - L)}{(L - C)(N \cdot R1/0.3333 - C)} \tag{5}$$

$$P2 = \frac{1000N(N \cdot R2/0.3333 - L)}{(L - C)(N \cdot R2/0.3333 - C)} \tag{6}$$

where C is the depth of anterior chamber (mm) as measured with an axial length ultrasound biometer or the like.

The astigmatic power P3 is the found from the above spherical power values, namely by subtracting D1 from D2. Thus, $$\begin{aligned} P3 &= P2 - P1 \\ &= \frac{1000N(N \cdot R2/0.3333 - L)}{(L - C)(N \cdot R2/0.3333 - C)} - \\ &\quad \frac{1000N(N \cdot R1/0.3333 - L)}{(L - C)(N \cdot R1/0.3333 - C)} \\ &= \frac{333.3N \cdot N(R2 - R1)}{(N \cdot R2 - 0.3333C)(N \cdot R1 - 0.3333C)} \end{aligned} \tag{7}$$

Now, when the strong principal meridian direction is used as the axis of astigmatism, P1 is taken as the intraocular lens spherical power and P3 as the intraocular lens astigmatic power.

On the other hand, when the weak principal meridian direction is used as the axis of astigmatism, P2 is taken as the intraocular lens spherical power and −P3 as the intraocular lens astigmatic power.

For example, when the strong principal meridian direction is horizontal with P1=25(D) and the weak principal meridian direction is vertical with P2=30(D), P3 is equal to P2−P1=5(D).

Therefore, the intraocular lens power S and the direction of the axis of astigmatism can be set in the following two ways.

(1) When the vertical direction is taken as the axis of astigmatism, the spherical power is +(D) and the astigmatic power is −5(D).

(2) When the horizontal direction is taken as the axis of astigmatism, the spherical power is +25(D) and the astigmatic power is +5(D).

In this manner, an intraocular lens capable of correcting preoperative astigmatism can be fabricated.

In a second procedure, the formula of Fyodorov is employed. Thus, spherical powers P1 and P2 are first calculated by means of equations (8) through (11).

$$P1 = \frac{N - L \cdot K1}{(L - C)(1 - C \cdot K1/N)} \tag{8}$$

$$P2 = \frac{N - L \cdot K2}{(L - C)(1 - C \cdot K2/N)} \tag{9}$$

$$K1 = \frac{1000(N - 1)}{R1} \tag{10}$$

$$K2 = \frac{1000(N - 1)}{R2} \tag{11}$$

Then, in the same manner as the procedure using the formula of Binkhorst, the intraocular lens power is calculated by adding astigmatic power P3 or −P3 to spherical power P1 or P2.

In a third procedure, the formula of Colenbrander is employed. Thus, spherical powers P1 and P2 are first calculated by equations (12) and (13).

$$P1 = \frac{N}{L-C} - \frac{N}{N/K1 - C} \quad (12)$$

$$P2 = \frac{N}{L-C} - \frac{N}{N/K2 - C} \quad (13)$$

Then, in the same manner as above, the intraocular lens power is found by adding astigmatic power P3 or −P3 to spherical power P1 or P2.

In a fourth procedure, the formula of van der Heijde is employed. Thus, using equations (14) and (15), spherical powers P1 and P2 are first calculated.

$$P1 = \frac{N}{L-C} - \frac{1}{(1/K1 - C/N)} \quad (14)$$

$$P2 = \frac{N}{L-C} - \frac{1}{(1/K2 - C/N)} \quad (15)$$

Thereafter, in the same manner as the procedure using the formula of Binkhorst, the intraocular lens power is found by adding astigmatic power P3 or −P3 to spherical power P1 or P2.

Incidentally since the first to fourth methods employing theoretical formulas can invariably be transformed to the following equations (16) and (17), spherical powers P1 and P2 may be computed by means of these equations.

$$P1 = \frac{N}{L-C} - \frac{N \cdot K1}{N - K1 \cdot C} \quad (16)$$

$$P2 = \frac{N}{L-C} - \frac{N \cdot K2}{N - K2 \cdot C} \quad (17)$$

Aside from the above embodiment, the intraocular lens power for a toric intraocular lens can be determined by the ray tracing error correcting (RTEC) technique as well.

In this last-mentioned procedure, the spherical powers in the strong and weak principal meridian directions of the cornea are determined by the RTEC technique and, then, the intraocular lens power is calculated in the same manner as the procedure using the formula of Binkhorst.

When the calculations of equations (1) through (17) are carried out with a computer, the intraocular lens power can be easily determined.

In accordance with the present invention, not only preoperative astigmatism but also operative astigmatism can be corrected in one operation.

In this case, the intraocular lens power is determined as follows.

First, operative astigmatism that will be prevailing approximately one year after operation is predicted. This predicted operative astigmatism and the preoperative astigmatism are summed to arrive at a total astigmatism power.

Then, based on this total astigmatism power, the intraocular lens power is calculated by any of the procedures described hereinbefore.

Man is born with slight astigmatism and, therefore, it is a physiological phenomenon that he tends to strain his eyes for a better imaging of the surroundings.

According to the present invention, it is possible to create a slight astigmatism which will take charge of the above physiological phenomenon rather than eliminating the astigmatism completely by means of an intraocular lens.

To determine the intraocular lens power for such an intraocular lens, the total astigmatic power is found by adding an intentional astigmatism to preoperative astigmatism and using this total astigmatic power, the intraocular lens power is calculated.

When the patient has myopia or hypermetropia, the spherical powers corrected for the myopia or hyermetropia are determined. When, with an intraocular lens inserted in one eye, myopia or hypermetropia will remain in the other eye, the correction of myopia or hypermetropia by the intraocular lens should be done by using spherical power values taking the balance between both eyes into consideration so that the myopia or hypermetropia will remain partially uncorrected in the operated eye.

I claim:

1. A method of determining the astigmatic power for a toric intraocular lens characterized by calculating an intraocular lens spherical power P1 from radius-of-corneal-curvature data R1 or corneal refractive power data K1 in the strong principal meridian direction, calculating the intraocular lens spherical power P2 from the radius-of-corneal-curvature data R2 or corneal refractive power data K2 in the weak principal meridian direction, subtracting P1 from P2 to find a cylindrical power P3, and taking P1 as the intraocular lens spherical power and P3 as the intraocular lens astigmatic power.

2. The method of determining the intraocular lens power for a toric intraocular lens as claimed in claim 1 which is characterized by using the formula $$P1 = \frac{N}{L-C} - \frac{N \cdot K1}{N - K1 \cdot C}$$

$$P2 = \frac{N}{L-C} - \frac{N \cdot K2}{N - K2 \cdot C}$$

$$K1 = \frac{1000(N - 1)}{R1}$$

$$K2 = \frac{1000(N - 1)}{R2}$$

where N: the refractive index of cornea, aqueous humor and vitreous body, L: axial length data (mm), C: anterior chamber depth data (mm), K1: corneal refractive power in the strong principal meridian direction, K2: corneal refractive power in the weak principal meridian direction, R1: radius-of-corneal-curvature data (mm) in the strong principal meridian direction, R2: radius-of-corneal-curvature data (mm) in the weak principal meridian direction, and P1 and P2: spherical power values.

3. The method of determining the intraocular lens power for a toric intraocular lens as claimed in claim 1 which is characterized by using the formula $$P1 = \frac{N - L \cdot K1}{(L - C)(1 - C \cdot K1/N)}$$

-continued
$$P2 = \frac{N - L \cdot K2}{(L - C)(1 - C \cdot K2/N)}$$

$$K1 = \frac{1000(N - 1)}{R1}$$

$$K2 = \frac{1000(N - 1)}{R2}$$

where N: the refractive index of cornea, aqueous humor and vitreous body, L: axial length data (mm), C: anterior chamber depth data (mm), K1: corneal refractive power in the strong principal meridian direction, K2: corneal refractive power in the weak principal meridian direction, R1: radius-of-corneal-curvature data (mm) in the strong principal meridian direction, R2: radius-of-corneal-curvature data (mm) in the weak principal meridian direction, and P1 and P2: spherical power values.

4. The method of determining the intraocular lens power for a toric intraocular lens as claimed in claim 1 which is characterized by using the formula $$P1 = \frac{N}{L - C} - \frac{N}{N/K1 - C}$$

$$P2 = \frac{N}{L - C} - \frac{N}{N/K2 - C}$$

$$K1 = \frac{1000(N - 1)}{R1}$$

$$K2 = \frac{1000(N - 1)}{R2}$$

where N: the refractive index of cornea, aqueous humor and vitreous body, L: axial length data (mm), C: anterior chamber depth data (mm), K1: corneal refractive power in the strong principal meridian direction, K2: corneal refractive power in the weak principal meridian direction, R1: radius-of-corneal-curvature data (mm) in the strong principal meridian direction, R2: radius-of-corneal-curvature data (mm) in the weak principal meridian direction, and P1 and P2: spherical power values.

5. The method of determining the intraocular lens power for a toric intraocular lens as claimed in claim 1 which is characterized by using the formula $$P1 = \frac{N}{L - C} - \frac{1}{(1/K1 - C/N)}$$

$$P2 = \frac{N}{L - C} - \frac{1}{(1/K2 - C/N)}$$

-continued
$$K1 = \frac{1000(N - 1)}{R1}$$

$$K2 = \frac{1000(N - 1)}{R2}$$

where N: the refractive index of cornea, aqueous humor and vitreous body, L: axial length data (mm), C: anterior chamber depth data (mm), K1: corneal refractive power in the strong principal meridian direction, K2: corneal refractive power in the weak principal meridian direction, R1: radius-of-corneal-curvature data (mm) in the strong principal meridian direction, R2: radius-of-corneal-curvature data (mm) in the weak principal meridian direction, and P1 and P2: spherical power values.

6. The method of determining the intraocular lens power for a toric intraocular lens as claimed in claim 1 which is characterized by using the formula $$P1 = \frac{1000N(N \cdot R1/0.3333 - L)}{(L - C)(N \cdot R1/0.3333 - C)}$$

$$P2 = \frac{1000N(N \cdot R2/0.3333 - L)}{(L - C)(N \cdot R2/0.3333 - C)}$$

where N: the refractive index of cornea, aqueous humor and vitreous body, L: axial length data (mm), C: anterior chamber depth data (mm), R1: radius-of-corneal-curvature data (mm) in the strong principal meridian direction, R2: radius-of-corneal-curvature data (mm) in the weak principal meridian direction, and P1 and P2: spherical power values.

7. The method of determining the intraocular lens power for a toric intraocular lens as claimed in claim 1 which is characterized by using the formula $$P1 = A - 2.5L - 0.9K1$$

$$P2 = A - 2.5L - 0.9K2$$

$$K1 = \frac{1000(N - 1)}{R1}$$

$$K2 = \frac{1000(N - 1)}{R2}$$

where A: an intraocular lens constant, N: the refractive index of cornea, aqueous humor and vitreous body, L: axial length data (mm), K1: corneal refractive power in the strong principal meridian direction, K2: corneal refractive power in the weak principal meridian direction, R1: radius-of-corneal-curvature data (mm) in the strong principal meridian direction, R2: radius-of-corneal-curvature data (mm) in the weak principal meridian direction, and P1 and P2: spherical power values.

* * * * *